US00PP29517P2

(12) United States Plant Patent
Stemkens

(10) Patent No.: US PP29,517 P2
(45) Date of Patent: Jul. 17, 2018

(54) ***VERBENA* PLANT NAMED 'VEAZ0042'**

(50) Latin Name: *Verbena hybrida*
Varietal Denomination: VEAZ0042

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,457

(22) Filed: Jun. 12, 2017

(51) Int. Cl.
*A01H 5/02* (2018.01)

(52) U.S. Cl.
USPC ..... Plt./308

(58) Field of Classification Search
USPC ..... Plt./308
See application file for complete search history.

(56) References Cited

PUBLICATIONS

PLUTO Plant Variety Database Mar. 8, 2018. p. 1.*

* cited by examiner

*Primary Examiner* — Annette H Para
(74) *Attorney, Agent, or Firm* — Dale Skalla

(57) ABSTRACT

A new *Verbena* plant named 'VEAZ0042' particularly distinguished by the its large purple red and light pink bicolored flowers, dark green foliage, and an upright plant habit.

1 Drawing Sheet

Latin name of the genus and species of the plant claimed: *Verbena hybrida.*

Varietal denomination: 'VEAZ0042'.

BACKGROUND OF THE NEW PLANT

The present invention comprises a new *Verbena*, botanically known as *Verbena hybrida*, and hereinafter referred to by the variety name 'VEAZ0042'.

'VEAZ0042' is a product of a planned breeding program. The new cultivar has large purple red and light pink bicolored flowers, dark green foliage, and an upright plant habit.

'VEAZ0042' originated from an open pollination which happened in July 2012 in the field in Enkhuizen, The Netherlands. The female parent is an unpatented proprietary plant designated 'R0802-1', having a red and white bicolored flower color and an upright plant habit The male parent of 'VEAZ0042' is unknown because the female was pollinated by a pollen-cloud of all plants in that field.

The resulting seed was sown in February 2013 in a greenhouse in Enkhuizen, The Netherlands. 'VEAZ0042' was selected as one flowering plant within the progeny of the stated cross in May 2013.

The first act of asexual reproduction of 'VEAZ0042' was accomplished when vegetative cuttings were propagated from the initial selection in June 2013 in a greenhouse in Enkhuizen, The Netherlands.

BRIEF SUMMARY OF INVENTION

Horticultural examination of plants grown from cuttings of the plant initiated in the spring of 2013, and continuing thereafter, has demonstrated that the combination of characteristics as herein disclosed for 'VEAZ0042' are firmly fixed and are retained through successive generations of asexual reproduction.

'VEAZ0042' has not been observed under all possible environmental conditions. The phenotype may vary significantly with variations in environment such as temperature, light intensity, and day length.

A Plant Breeder's Right for this cultivar was applied for in the European Union on Sep. 20, 2016, No. 2016/2278. 'VEAZ0042' has not been made publicly available prior to the effective filing date of this application, notwithstanding any disclosure that may have been made less than one year prior to the effective filing date of this application by the inventor or another who obtained 'VEAZ0042' directly from the inventor.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawings show typical flower and foliage characteristics of 'VEAZ0042' with colors being as true as possible with an illustration of this type.

Figure 1:
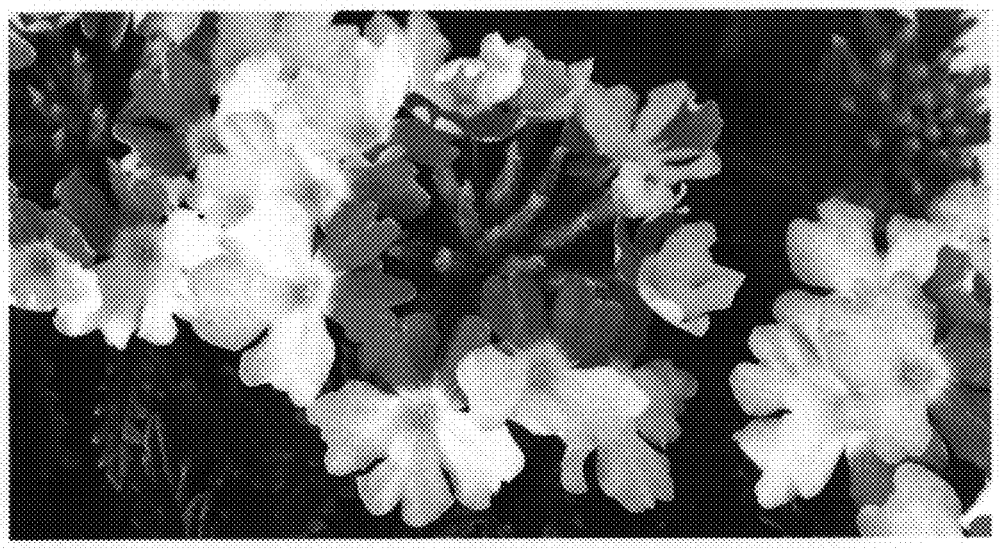
Figure 2:
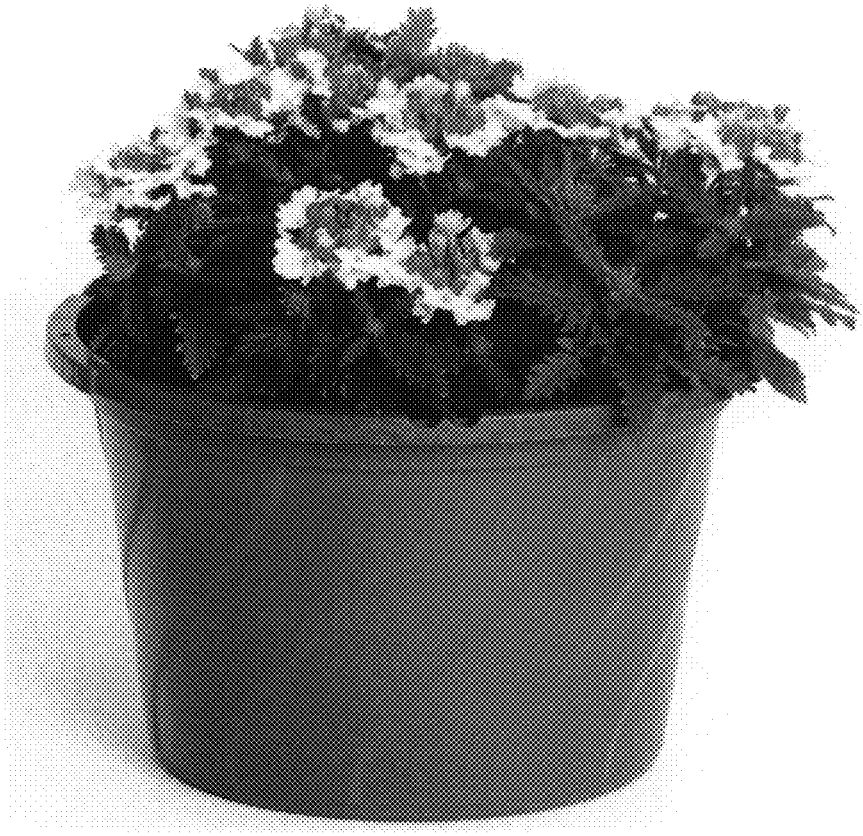

The photographic drawing in FIG. 1 shows a close view of an inflorescence, and in FIG. 2 a whole flowering plant.

DETAILED BOTANICAL DESCRIPTION

The first plant description and measurements were made in Andijk, The Netherlands in late April 2017 using potted plants on benches in the greenhouse.

The aforementioned photographs were taken on April 2017 in Gilroy, Calif., USA. The same greenhouse plants were used, as described above.

Color references are made to The Royal Horticultural Society Colour Chart (R.H.S.) 2001.

TABLE 1

DIFFERENCES BETWEEN THE NEW VARIETY 'VEAZ0042' AND A MOST SIMILAR VARIETY

| | 'VEAZ0042' | 'Flagdena' (U.S. Plant Pat. No. 22,438) |
|---|---|---|
| Flower color, upper petals: | RHS 67B to RHS 67C | RHS N57B |
| Flower color, lower petals: | RHS N66D with white | RHS 61D edges and white |
| Inflorescence diameter: | 4 cm | 5 cm |
| Growth habit: | Upright | Trailing |

Plant:

*Form, growth and habit.*—Herbaceous, upright growing; vigorous and free-branching.

*Plant height.*—18.0 cm.

*Plant height (inflorescence included).*—22.0 cm.

*Plant width.*—28.0 cm.

Roots:

*Number of days to initiate and produce roots.*—10-14 days at about 22 degrees C.

*Type.*—Fine, fibrous, free branching.

*Color.*—RHS N155B but whiter.

Foliage:

*Arrangement.*—Opposite, simple.

*Immature, leaf color, upper surface.*—RHS 138B.

*Immature, leaf color, lower surface.*—RHS 137C.

*Mature, leaf color, upper surface.*—RHS 137A.

*Mature, leaf color, lower surface.*—RHS 147B.

*Length.*—About 4 cm.

*Width.*—3.0-3.4 cm.

*Shape.*—Ovate to hastate.

*Base shape.*—Cordate.

*Apex shape.*—Acute.

*Margin.*—Dentate.

*Texture, upper surface.*—Hirsute.

*Texture, lower surface.*—Hirsute.

*Color of veins, upper surface.*—RHS 144B.

*Color of veins, lower surface.*—RHS 144B.

*Pattern of veining.*—Pinnate.

*Petiole color.*—From RHS 145C (near upper end) to RHS 145D at base.

*Petiole length.*—1.1 cm.

*Petiole width.*—0.2 cm.

*Texture.*—Hirsute.

Stem:

*Branching characteristics.*—Side branches are potentially developed at every node.

*Quantity of main branches per plant.*—About 17.

*Color of stem.*—RHS 146A.

*Stem length.*—About 15 to 17 cm.

*Stem width.*—About 0.35 cm.

*Length of internodes.*—2.5-4.5 cm.

*Texture.*—Hirsute.

*Color of peduncle.*—RHS 138B.

*Length of peduncle.*—About 2-4 cm.

*Peduncle diameter.*—0.2 cm.

*Texture.*—Canescent.

Inflorescence

*Type.*—Umbel-like, but actually a spike, umbrella-shaped, large.

*Blooming habit.*—Flowers continuously through the summer months.

*Lastingness of individual blooms on the plant.*—About 6 days in the greenhouse.

*Fragrance.*—Slight musky.

*Number of inflorescences per plant.*—40 to 50 at various stages.

*Horizontal diameter of inflorescence.*—About 4.5 cm.

*Depth of inflorescence.*—4.0 cm.

*Number of florets per inflorescence (including any buds at the time).*—35-38.

Bud (just when opening/showing color):

*Color.*—RHS 62D.

*Length.*—0.4 cm.

*Width.*—0.4 cm.

*Shape.*—Tubular with a bulbous end.

Floret:

*Form.*—Sessile; salver-shape, composed of 5 partly fused petals with a base of a narrow tube.

*Immature color, upper surface, upper petals.*—RHS 59D with shades of RHS 67B.

*Immature color, upper surface, lower petals.*—Whitish, RHS 150C to RHS155A at center with RHS N66D (purple-pink) edges.

*Immature color, lower surface, upper petals.*—RHS N66D.

*Immature color, lower surface, lower petals.*—RHS 155A (white).

*Mature color, upper surface, upper petals.*—RHS 59C with shades of RHS 67C.

*Mature color, upper surface, lower petals.*—Whitish, RHS 155A at center with RHS N66C (purple-pink) edges.

*Mature color, lower surface, upper petals.*—RHS N66D.

*Mature color, lower surface, lower petals.*—RHS 155A (white).

*Floret diameter.*—2.0-2.2 cm.

*Floret length (depth).*—2.0-2.1 cm.

*Petal length.*—1.1 cm.

*Petal width.*—0.7 cm.

*Shape.*—Obcordate.

*Apex shape.*—Emarginate.

*Margin.*—Entire.

*Petal texture, upper surface.*—Papillose; glabrous.

*Petal texture, lower surface.*—Papillose, sparce hair, a few glandular hairs.

*Corolla tube length.*—1.8 cm.

*Corolla tube width.*—0.2 cm.

*Corolla tube color inside.*—RHS 150D.

*Tube color outside.*—RHS 145D near corolla to RHS150D at base.

*Corolla texture, inside.*—Papillose, short hair with a few longer hairs.

*Corolla texture, outside.*—Glabrous at base, upper part canescent.

*Throat hair color.*—RHS 155D but whiter.

Calyx:

*Type.*—Five sepals whose margins are fused to each other along their length, with a transparent membrane of less than 0.1 cm in width and with one smaller sepal attached to the base of the calyx.

*Color of sepals.*—RHS 138B.

*Length of sepals.*—1.2 cm.

*Width of sepals.*—0.2 cm.

*Sepal shape*.—Linear, but fused.
*Apex shape*.—Acute.
*Margins*.—Entire.
*Texture*.—Densely covered with short hair and many glandular hairs.

Reproductive organs:
*Gynoecium*.—
*Pistil*.—1.
*Pistil length*.—1.6 cm.
*Style color*.—RHS N144D.
*Style length*.—1.5 cm.
*Stigma color*.—RHS 144A.
*Ovary color*.—RHS 144B.
*Ovary length*.—0.25 cm.
*Ovary width*.—0.1 cm.
*Androecium*.—
*Stamens*.—Anthers and filaments fused to upper half of corolla tube; four anthers with two pollen sacs per anther.
*Color of filaments*.—RHS 151D.
*Filament length*.—0.2 cm.
*Anther color*.—RHS 151D.
*Anther length*.—0.15 cm.
*Pollen amount*.—None observed.

Fertility/seed set: Neither seed nor fruit production has been observed.

Disease/pest resistance: Resistance to pathogens and pests common to *Verbena* has not been observed.

What is claimed is:

1. A new and distinct variety of *Verbena* plant named 'VEAZ0042' substantially as illustrated and described herein.

* * * * *